(12) United States Patent
Hasegawa et al.

(10) Patent No.: US 10,306,741 B2
(45) Date of Patent: May 28, 2019

(54) ILLUMINATION SYSTEM AND MOBILE BODY

(71) Applicant: PANASONIC INTELLECTUAL PROPERTY MANAGEMENT CO., LTD., Osaka (JP)

(72) Inventors: Junichi Hasegawa, Osaka (JP); Kazuhiro Hatta, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/925,130

(22) Filed: Mar. 19, 2018

(65) Prior Publication Data

US 2018/0288862 A1  Oct. 4, 2018

(30) Foreign Application Priority Data

Mar. 29, 2017  (JP) ................. 2017-065606

(51) Int. Cl.
*H05B 37/02* (2006.01)
*H05B 33/08* (2006.01)
*A61M 21/02* (2006.01)
*A61M 21/00* (2006.01)

(52) U.S. Cl.
CPC ..... *H05B 37/0281* (2013.01); *A61M 21/0094* (2013.01); *A61M 21/02* (2013.01); *H05B 33/086* (2013.01); *H05B 33/0845* (2013.01); *H05B 33/0863* (2013.01); *H05B 37/0227* (2013.01); *H05B 37/0272* (2013.01); *A61M 2021/0044* (2013.01); *A61M 2021/0083* (2013.01); *A61M 2205/50* (2013.01)

(58) Field of Classification Search
CPC .............. H05B 33/0845; H05B 33/086; H05B 37/0227; H05B 37/0245; H05B 37/0281; H05B 37/029
USPC ........................................ 315/308, 312, 360
See application file for complete search history.

(56) References Cited

U.S. PATENT DOCUMENTS

| 2012/0043910 | A1* | 2/2012 | Nagashima | ........ H05B 37/0227 315/294 |
| 2012/0153837 | A1* | 6/2012 | Park | ................... H05B 33/0869 315/151 |
| 2013/0088168 | A1* | 4/2013 | Mohan | ................... G05B 15/02 315/297 |
| 2013/0141013 | A1* | 6/2013 | Kodama | ............ H05B 33/0857 315/294 |
| 2016/0074620 | A1 | 3/2016 | Toda et al. | |

(Continued)

FOREIGN PATENT DOCUMENTS

| JP | 2011-023339 A | 2/2011 |
| JP | 2013-191513 A | 9/2013 |

(Continued)

*Primary Examiner* — Tung X Le
(74) *Attorney, Agent, or Firm* — McDermott Will & Emery LLP

(57) ABSTRACT

An illumination system includes: an illumination device; a time setter that sets a target time; and a controller that controls a color temperature of light emitted by the illumination device. The controller determines a target color temperature according to the target time, and causes the color temperature of the light emitted by the illumination device to be the target color temperature at the target time.

12 Claims, 7 Drawing Sheets

(56) References Cited

U.S. PATENT DOCUMENTS

2016/0133229 A1* 5/2016 Inoe .................. G09G 5/026
 345/690
2018/0077783 A1* 3/2018 Sooch ................ H05B 33/0863

FOREIGN PATENT DOCUMENTS

| JP | 2014-143207 A | 8/2014 |
| JP | 2016-058345 A | 4/2016 |

* cited by examiner

ILLUMINATION SYSTEM AND MOBILE BODY

CROSS REFERENCE TO RELATED APPLICATION

This application claims the benefit of priority of Japanese Patent Application Number 2017-065606 filed on Mar. 29, 2017, the entire content of which is hereby incorporated by reference.

BACKGROUND

1. Technical Field

The present disclosure relates to an illumination system that supports a user's awakening, and a mobile body that uses the illumination system.

2. Description of the Related Art

Conventionally, an illumination system including an illuminator that emits illumination light and a controller that controls the illumination state of the illuminator is known. To provide a user with a pleasant lighting environment during sleep hours, the illumination system starts emitting light before the user's wake-up time and changes the dimming rate in a stepwise manner until the wake-up time (see Japanese Unexamined Patent Application Publication No. 2013-191513, for example).

SUMMARY

With such an illumination system that merely lightens the user's sleep, the user may not feel good after being woken up, in terms of the biological rhythm.

The present disclosure provides an illumination system and a mobile body that provide a lighting environment appropriate to a user after wake-up, in terms of the biological rhythm.

An illumination system according to an aspect of the present disclosure includes: an illumination device; a time setter that sets a target time; and a controller that controls a color temperature of light emitted by the illumination device. The controller determines a target color temperature according to the target time, and causes the color temperature of the light emitted by the illumination device to be the target color temperature at the target time.

Furthermore, a mobile body according to an aspect of the present disclosure includes the illumination system.

The present disclosure provides a lighting environment appropriate to a user after wake-up, in terms of the biological rhythm.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF EMBODIMENT(S)

Outline

It has been known recently that being irradiated with light having high illuminance from the morning to about 15:00 adjusts the biological rhythm such as the melatonin secretion rhythm and the circadian rhythm, thereby improving and alleviating symptoms such as disturbed circadian rhythm, sleepiness, and insomnia. Here, the biological rhythm is a cycle of about one day in which, as physiological phenomena, a person becomes sleepy at a certain time and naturally wakes up after sleeping for a certain time period.

Figure 10:
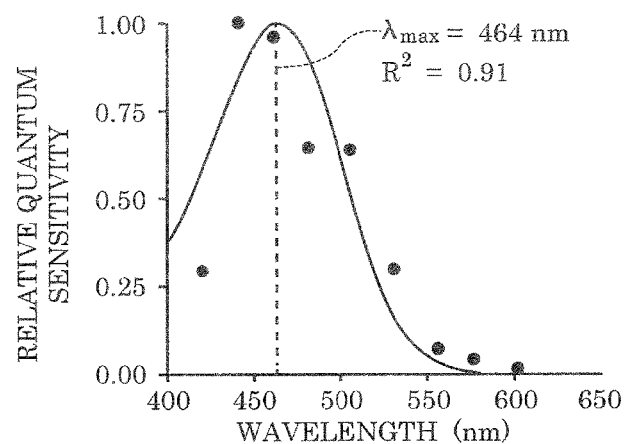
FIG. 10 is a graph illustrating an action curve for suppression of melatonin secretion.

An amount of secreted melatonin is one of the indices for evaluation of the biological rhythm. That there is an action curve for the amount of secreted melatonin is indicated in G. C. Brainard, J. P. Hanifin, J. M. Greeson, B. Byrne, G. Glickman, E. Gerner and M. D. Rollag, "Action spectrum for melatonin regulation in humans: evidence for a novel circadian photoreceptor", J Neurosci, 21, pp. 6405-6412 (2001). FIG. 10 is a graph illustrating an action curve for suppression of melatonin secretion. In FIG. 10, the vertical axis indicates relative sensitivity, and the horizontal axis indicates wavelength. As illustrated in FIG. 10, the relative sensitivity has a peak at the wavelength of about 464 nm.

Melatonin, which has a sleep-inducing effect, generally tends to be secreted in body in high volume in the nighttime and secreted in less volume in the morning and the daytime. The curve illustrated in FIG. 10 shows that the suppression of melatonin secretion is caused by light in the blue region. Thus, in the nighttime, it is desirable to reduce light in the blue region that suppresses melatonin secretion, so as to promote the user's sleep. On the other hand, in the morning and the daytime, it is desirable to increase light in the blue region that suppresses melatonin secretion, so as to awake the user.

Here, taking into consideration that light having a high color temperature contains a high proportion of light in the blue region whereas light having a low color temperature contains a low proportion of light in the blue region, it is considered possible to adjust the biological rhythm by emitting light having an appropriate color temperature at an appropriate time.

In view of this, this illumination system starts increasing gradually the output and the color temperature of light before a target time at which the user is to wake up, so that the user's sleep state is gradually lightened toward the target time that is a wake-up time, thereby allowing the user to wake up pleasantly.

Figure 11:
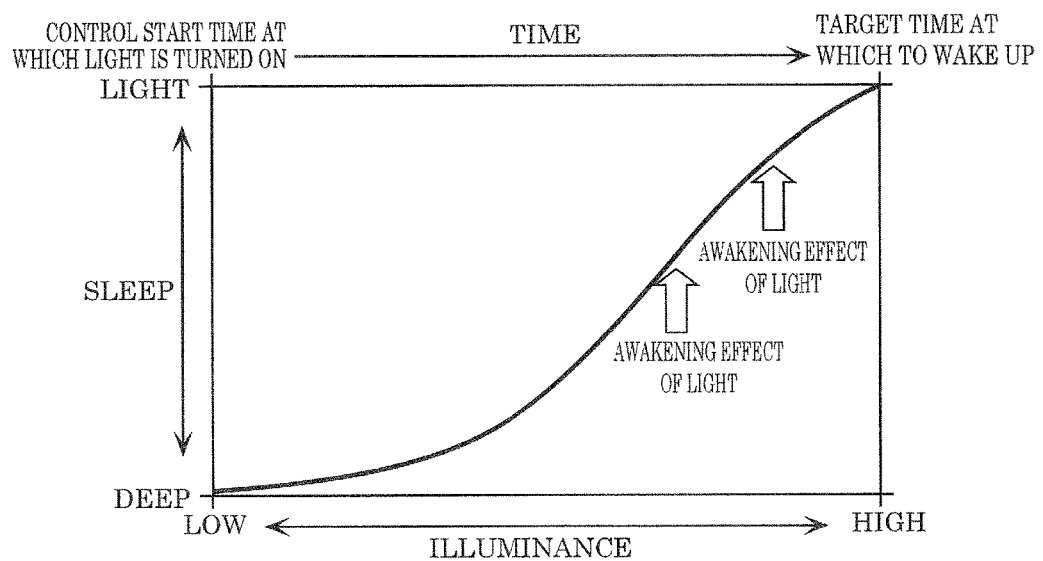
FIG. 11 is an explanatory diagram illustrating a relationship between emitted light and sleep.

FIG. 11 is an explanatory diagram illustrating a relationship between emitted light and sleep.

It can be seen from FIG. 11 that sleep makes a gradual transition from a deep sleep state to a light sleep state as the illuminance increases. An increased illuminance produces an awakening effect on the user, and the highest illuminance brings about a light sleep state, allowing the user to wake up pleasantly.

In view of the above, the present disclosure provides an illumination system and a mobile body that provide a lighting environment appropriate to a user after wake-up, in terms of the biological rhythm.

Hereinafter, an embodiment is described with reference to the drawings. Note that the following embodiment describes a general or specific example. The numerical values, shapes, materials, structural elements, the arrangement and connection of the structural elements, steps, the processing order of the steps, etc., illustrated in the following embodiment are mere examples, and are therefore not intended to limit the present disclosure. Furthermore, among the structural elements in the following embodiment, those not recited in any one of the independent claims representing the most generic concepts are described as optional structural elements.

Note also that each figure is a schematic illustration and not necessarily a precise illustration. Furthermore, throughout the figures, the same reference signs are given to essentially the same structural elements, and redundant descriptions may be omitted or simplified.

Embodiment

[Configuration]

Figure 1:
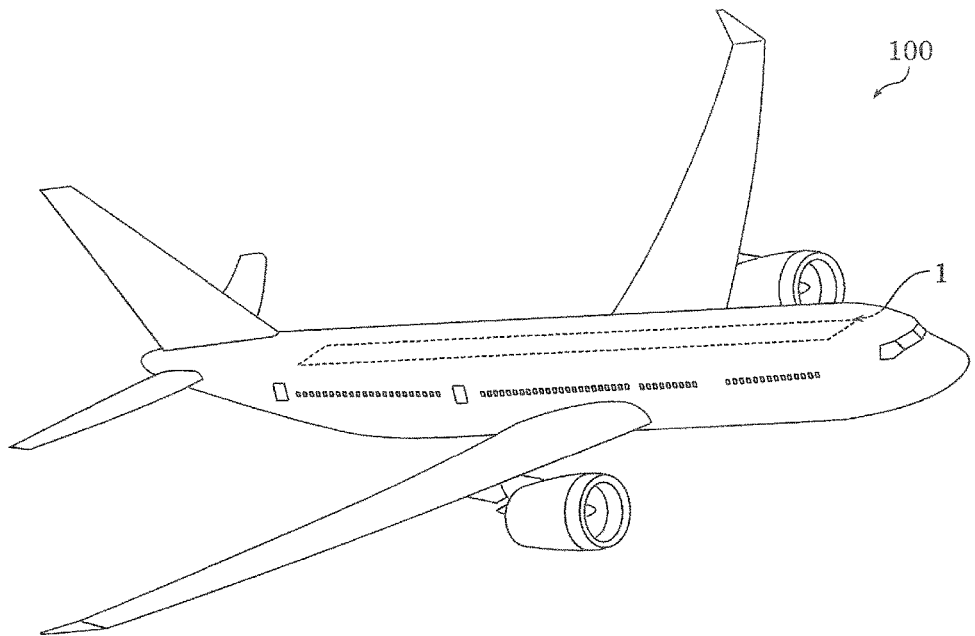
FIG. 1 is an external view illustrating an aircraft including an illumination system according to an embodiment.
Figure 2:
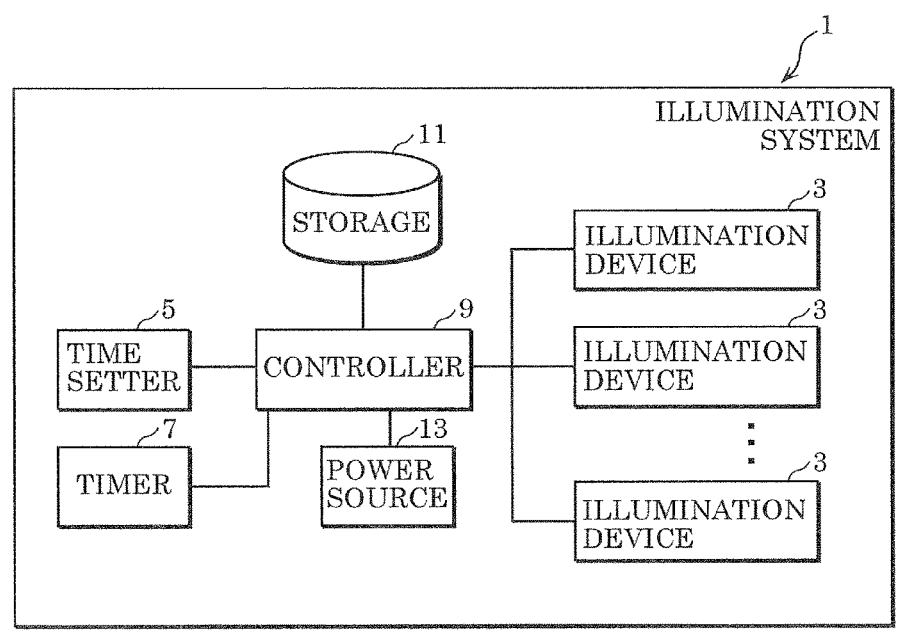
FIG. 2 is a block diagram illustrating the illumination system according to the embodiment.

FIG. 1 is an external view illustrating an aircraft including illumination system 1 according to the present embodiment. FIG. 2 is a block diagram illustrating illumination system 1 according to the present embodiment.

As illustrated in FIG. 1 and FIG. 2, illumination system 1 according to the present embodiment includes a plurality of illumination devices 3 disposed inside mobile body 100 such as an aircraft. Illumination devices 3 are typically disposed in the ceiling of the aircraft.

Illumination system 1 includes the plurality of illumination devices 3, time setter 5, timer 7, controller 9, storage 11, and power source 13.

Illumination devices 3 are disposed in a part of a construction such as a side wall or a part of a ceiling. Illumination devices 3 are what is known as the main illumination (direct illumination), and may emit light to illuminate the aircraft's entire interior or illuminate each seat. Light emission of illumination devices 3 is controlled by controller 9. Each illumination device 3 specifically includes a light emitter.

The light emitter is, for example, a light-emitting module using a light-emitting diode (LED) as a light-emitting element, and emits light such as white light. The light-emitting element may be what is known as a surface mount device (SMD) LED element. Further, the light emitter is a light-emitting module which includes a plurality of types of light-emitting elements that emit light having mutually different colors (color temperatures), and on which dimming control and toning control can be performed by controller 9 adjusting the amount of power supplied from power source 13.

Time setter 5 is a device capable of setting a plurality of target times. Time setter 5 sets each target time through a user's operation on a button, a switch, or a touch panel, for example.

Here, examples of the target time include a wake-up time at which the user intends to wake up, a meal time at which the user intends to have a meal, a bedtime at which the user intends to start having a sleep, and an estimated time of arrival at which mobile body 100 is estimated to arrive at a destination. As such, target times are set for various purposes for which certain actions are taken. Note that since a target time is set for each of various purposes, the purposes are not limited to wake-up, meal, sleep, arrival at the destination, etc. Note that instead of setting a target time, time setter 5 may set a period of time from, for example, a bedtime or a current time to a wake-up time.

Timer 7 is electrically connected to controller 9 and outputs information indicating a current time to controller 9.

Controller 9 controls the color temperature of light emitted by illumination devices 3. Specifically, controller 9 controls operations of the light emitter such as turning the light on, turning the light off, dimming, and toning, according to a control signal received via an operation unit such as a remote control. The control on the operations such as dimming and toning is to adjust the color or the color temperature of light to be emitted by the light emitter. Controller 9 performs dimming control on a light source, that is, increases or decreases the brightness of light emitted by the light emitter by controlling a driver, for example. Controller 9 includes, for example, a circuit for controlling an element such as the light emitter.

When a plurality of target times are set by time setter 5, controller 9 determines a target color temperature according to a target time selected from among the plurality of target times, and causes the color temperature of the light emitted by illumination devices 3 to be the determined target color temperature at the selected target time. Specifically, controller 9 selects a subsequent target time from among the plurality of target times based on the information indicating the current time received from timer 7, and causes the color temperature of the light emitted by illumination devices 3 to be the target color temperature at the selected target time. The relationship between the target time and the color temperature may be indicated in a preset table. For example, a target color temperature may be determined based on a table indicating color temperatures corresponding to the seasons at the destination and the target times. The table may be stored in storage 11 or may be stored in a memory included in controller 9.

Controller 9 determines a control period based on a time period from the current time received from timer 7 to the selected target time. Here, the control period is a time period from a control start time at which illumination devices 3 start emitting light to the target time.

Controller 9 performs color temperature increase control of increasing the color temperature of the light emitted by illumination devices 3 to the target color temperature with a lapse of time. Specifically, in the environment where illumination devices 3 are turned off because the user is asleep etc., controller 9 turns on illumination devices 3 at a time preceding the target time by the control period, and increases the color temperature of the light emitted by illumination devices 3 with a lapse of time so that the color temperature reaches the target color temperature at the target time.

After performing the color temperature increase control, controller 9 performs color temperature maintaining control of maintaining the color temperature of the light emitted by illumination devices 3 at the target color temperature. That is to say, after increasing the color temperature of the light emitted by illumination devices 3 to the target color temperature, controller 9 causes illumination devices 3 to continue emitting the light having the target color temperature. The time period during which the target color temperature of the light emitted by illumination devices 3 is maintained may finish when controller 9 starts causing the color temperature to be the subsequent target color temperature.

Controller 9 determines the brightness of the light emitted by illumination devices 3 according to the target time, and controls the brightness of the light emitted by illumination devices 3 accordingly. Controller 9 performs output increase control of increasing the brightness of the light emitted by illumination devices 3 to a target output with a lapse of time. In the present embodiment, when performing the output increase control, controller 9 gradually increases the brightness of the light emitted by illumination devices 3 with a lapse of time so that the brightness reaches the target output at the target time. That is to say, based on the information indicating the current time received from timer 7, controller 9 turns on illumination devices 3 at the control start time preceding the target time by the control period, and gradually increases the output of illumination devices 3 with a lapse of time. To gradually increase the output of illumination devices 3 means to gradually increase the brightness of the light emitted by illumination devices 3. The output increase control is performed by controller 9 in an environment where, for example, illumination devices 3 are turned off because the user is asleep etc. Note that the output increase control may start simultaneously with the color temperature increase control, but need not start simultaneously with the color temperature increase control.

Here, the target output is a preset brightness of the light emitted by illumination devices 3, and may be freely set via a setter not illustrated. The target output may be set for each target time.

Before performing the color temperature increase control, controller 9 performs weak lighting control of causing illumination devices 3 to emit light having a brightness lower than the target output and a color temperature lower than the target color temperature. In other words, controller 9 performs the weak lighting control, and subsequently performs the color temperature increase control. Here, the weak lighting control is to cause illumination devices 3 to emit light having an output of 15% or less of the target output of the light emitted by illumination devices 3, for example.

Controller 9 calculates a sleep period from the bedtime to the target time using timer 7, and determines, within a time period from the current time to the target time, a time period during which the weak lighting control is to be performed, based on the sleep period. Specifically, controller 9 performs the weak lighting control for a first period when the time period from the current time to the target time is longer than or equal to a predetermined period. Controller 9 performs the weak lighting control for a second period shorter than the first period when the time period from the current time to the target time is shorter than the predetermined period. Here, the first period and the second period are time periods shorter than the time period from the current time to the target time. Note that although, in the present embodiment, the first period or the second period is determined using the predetermined time period as a threshold, controller 9 may set the time period in which the weak lighting control is to be performed in proportion to the time period from the current time to the target time, for example.

Storage 11 is a storage device that is electrically connected to controller 9 and stores a target time received from time setter 5, a target output, and a target color temperature, for example. Storage 11 is implemented by a semiconductor memory, for example.

Power source 13 includes a power source circuit that generates power for causing each light emitter to emit light. For example, power source 13 converts power supplied from a power system into direct-current power at a predetermined level through rectification, smoothing, voltage drop, etc., and supplies each light emitter with the direct-current power.

[Operation]

Figure 3:
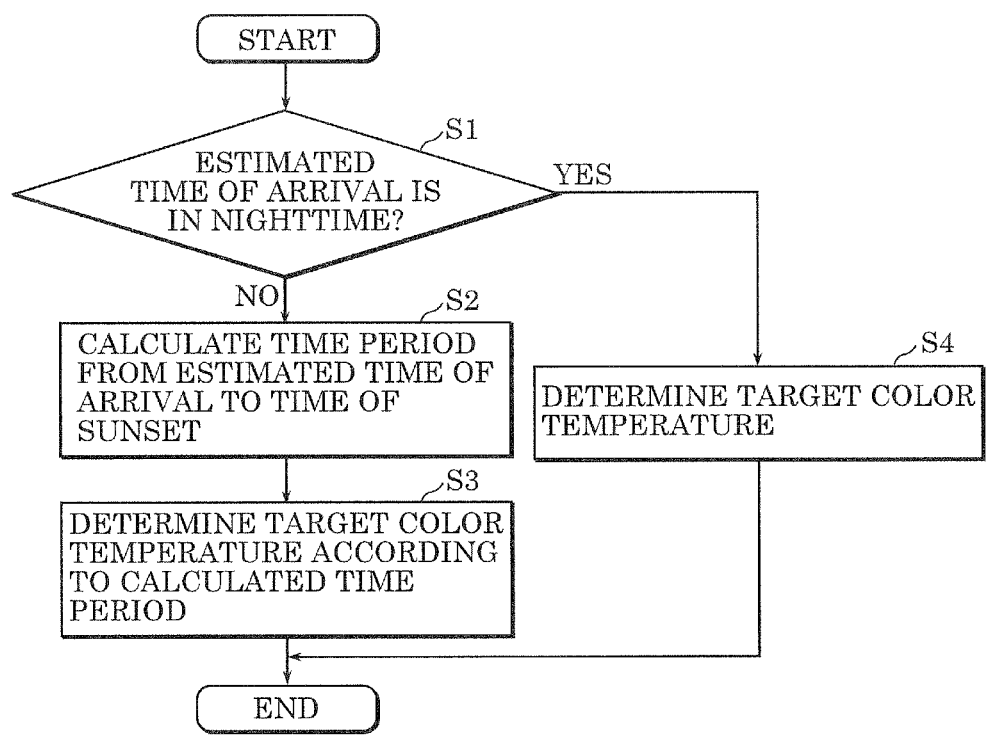
FIG. 3 is a flow chart for determining a target color temperature according to an estimated time of arrival in the illumination system according to the embodiment.
Figure 4:
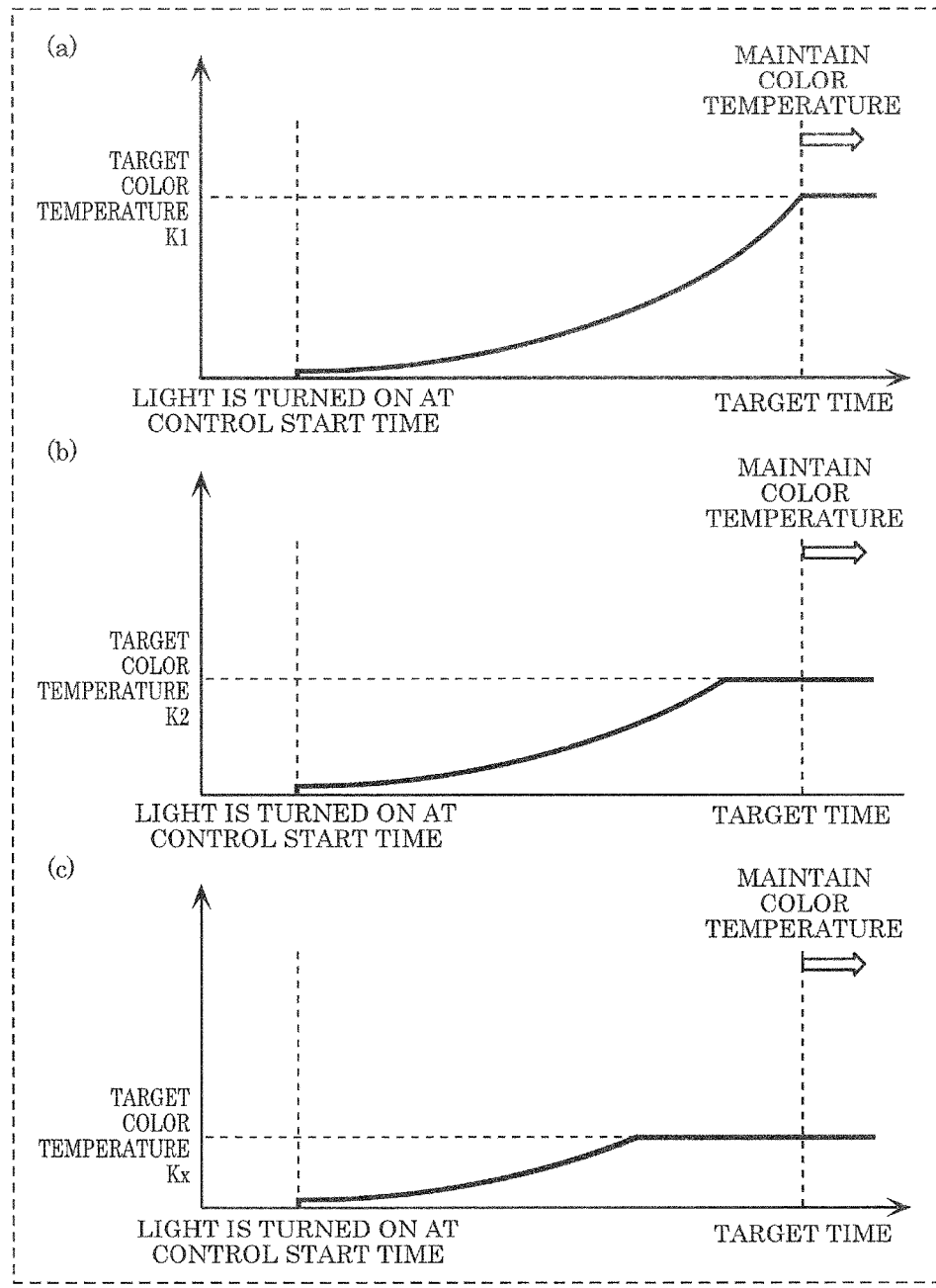
FIG. 4 is an explanatory diagram illustrating target color temperatures each determined according to an estimated time of arrival in the illumination system according to the embodiment.

The following describes operations of illumination system 1 according to the present embodiment with reference to FIG. 3 and FIG. 4.

FIG. 3 is a flow chart for determining a target color temperature according to an estimated time of arrival in illumination system 1 according to the present embodiment. FIG. 4 is an explanatory diagram illustrating target color temperatures each determined according to an estimated time of arrival in illumination system 1 according to the present embodiment.

Here, the color temperature of light to be emitted by illumination devices 3 at the target time is determined depending on whether the time at the destination of mobile body 100 when mobile body 100 arrives at the destination is the daytime or nighttime.

As illustrated in FIG. 3, first, controller 9 determines whether or not the estimated time of arrival is within a time period from the time of sunrise at the destination to the time of sunset at the destination. In other words, controller 9 determines whether the estimated time of arrival of mobile body 100 is in the nighttime or daytime (S1).

When determining that the estimated time of arrival of mobile body 100 is in the nighttime (YES in S1), controller 9 determines a target color temperature. That is to say, when performing the color temperature increase control and the color temperature maintaining control, controller 9 causes each illumination device 3 to emit light having the determined target color temperature (S4). Then, the flow is finished.

In Step S4, controller 9 determines the target color temperature based on a relationship between a time period from the estimated time of arrival to the time of sunrise at the destination and a time period from the time of sunset at the destination to the estimated time of arrival. Specifically, controller 9 decreases the target color temperature as the time period from the estimated time of arrival to the time of sunrise at the destination becomes longer than the time period from the time of sunset at the destination to the estimated time of arrival. Controller 9 determines, as the target color temperature, the lowest one of the target color temperatures set in a day, when the time period from the time of sunset at the destination to the estimated time of arrival is approximately equal to the time period from the estimated time of arrival to the time of sunrise at the destination. Further, controller 9 increases the target color temperature as the time period from the estimated time of arrival to the time of sunrise at the destination becomes shorter than the time period from the time of sunset at the destination to the estimated time of arrival.

Note that when the time period from the estimated time of arrival to the time of sunrise at the destination is longer than the time period from the time of sunset at the destination to the estimated time of arrival, it means that the estimated time of arrival of mobile body 100 is within a time period from the sunset to midnight, for example. Further, when the time period from the time of sunset at the destination to the estimated time of arrival is approximately equal to the time period from the estimated time of arrival to the time of sunrise at the destination, it means that the estimated time of arrival of mobile body 100 is midnight, for example. Furthermore, when the time period from the estimated time of arrival to the time of sunrise at the destination is shorter than the time period from the time of sunset at the destination to the estimated time of arrival, it means that the estimated time of arrival of mobile body 100 is within a time period from the midnight to the dawn, for example.

Next, when determining that the estimated time of arrival of mobile body 100 is in daytime (NO in S1), controller 9 calculates a time period from the estimated time of arrival to the time of sunset (S2).

Next, controller 9 determines the target color temperature according to the time period calculated in Step S2 (S3). Specifically, when the estimated time of arrival is within the time period from the time of sunrise at the destination to the time of sunset at the destination, controller 9 decreases the target color temperature according to the time period from the estimated time of arrival to the time of sunset. For example, when the estimated time of arrival is the time of sunrise, controller 9 determines, as the target color temperature, the highest one of the target color temperatures set in a day, and decreases the target color temperature with a lapse of time from the time of sunrise. When the estimated time of arrival is within the time period from the time of sunset at the destination to the time of sunrise at the destination, controller 9 causes the color temperature of the light emitted by illumination devices 3 to be the target color temperature. Then, the flow is finished.

The target color temperature determined in Step S3 illustrated in FIG. 3 is specifically described with reference to FIG. 4. (a) of FIG. 4 is an explanatory diagram illustrating the color temperature when the time period from the estimated time of arrival to the time of sunset is long. (b) of FIG. 4 is an explanatory diagram illustrating the color temperature when the time period from the estimated time of arrival to the time of sunset is short. (c) of FIG. 4 is an explanatory diagram illustrating the color temperature when the estimated time of arrival is in the nighttime. That the time period from the estimated time of arrival to the time of sunset is long may mean, for example, that the time period from the estimated time of arrival to the time of sunset accounts for at least half of the time period from the time of sunrise to the time of sunset, or may mean that the time period from the estimated time of arrival to the time of sunset is longer than or equal to a predetermined period. That the time period from the estimated time of arrival to the time of sunset is short may mean, for example, that the time period from the estimated time of arrival to the time of sunset accounts for less than half of the time period from the time of sunrise to the time of sunset, or may mean that the time period from the estimated time of arrival to the time of sunset is shorter than the predetermined period.

As illustrated in (a) and (c) of FIG. 4, when the time period from the estimated time of arrival to the time of sunset is long, target color temperature K1, which is higher than target color temperature Kx determined when the estimated time of arrival is in the nighttime, is determined as the target color temperature. When performing the color temperature increase control and the color temperature maintaining control, controller 9 causes each illumination device 3 to emit light having target color temperature K1.

As illustrated in FIG. (b) and (c) of FIG. 4, when the time period from the estimated time of arrival to the time of sunset is short, target color temperature K2 is determined as the target color temperature. Here, target color temperature K2 is lower than target color temperature K1 and higher than target color temperature Kx determined when the estimated time of arrival is in the nighttime. As illustrated in FIG. (a) and (b) of FIG. 4, when performing the color temperature increase control and the color temperature maintaining control, controller 9 causes each illumination device 3 to continue emitting light having target color temperature K1 or K2. Note that target color temperatures K1 and K2 are mere examples, and the target color temperature is not limited to these.

Next, the lighting control performed by controller 9 on each illumination device 3 is described with reference to FIG. 5 and FIG. 6.

Figure 5:
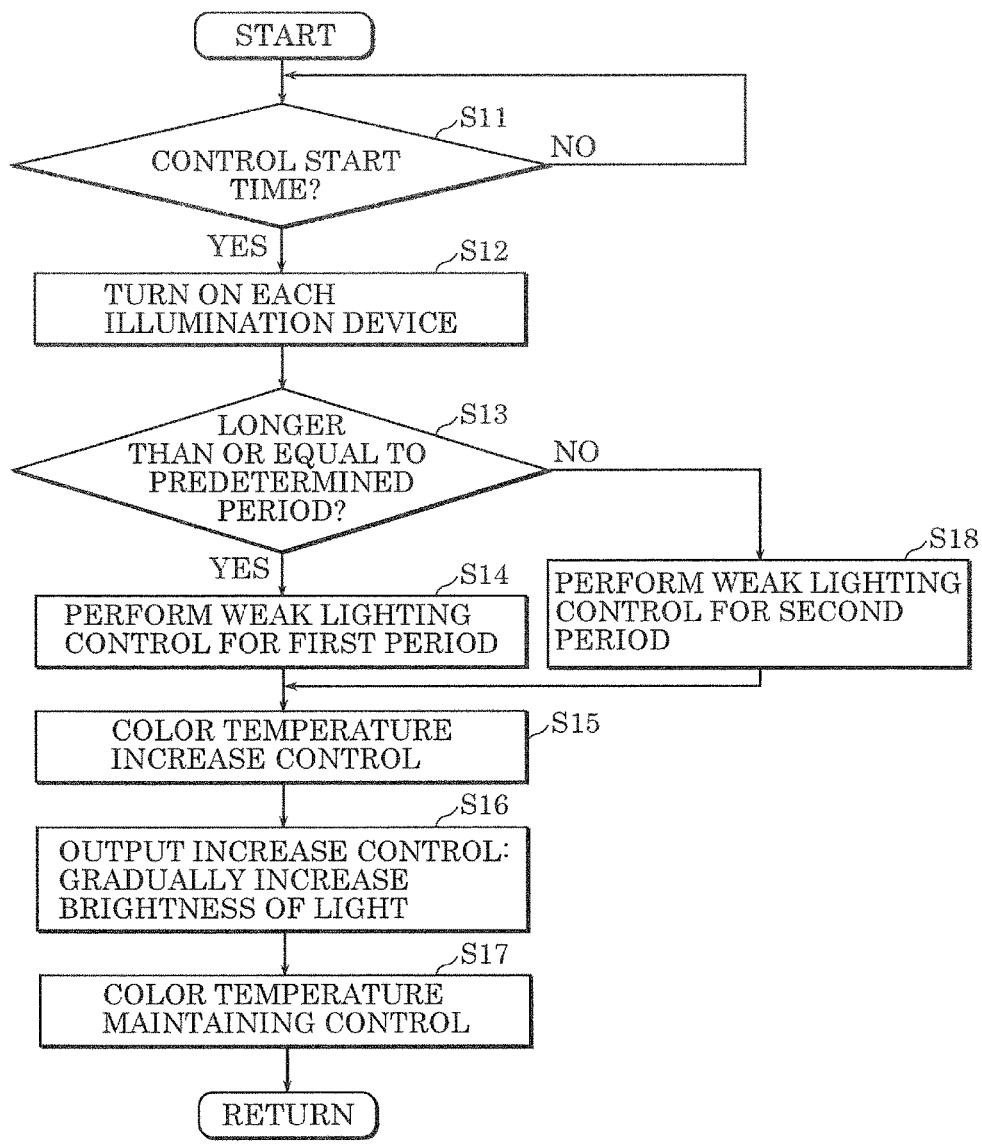
FIG. 5 is a flow chart illustrating operations of each illumination device included in the illumination system according to the embodiment.

FIG. 5 is a flow chart illustrating operations of each illumination device 3 included in illumination system 1 according to the present embodiment. FIG. 6 is an explanatory diagram illustrating the color temperature and the brightness of light emitted by each illumination device 3 included in illumination system 1 according to the present embodiment.

Figure 6:
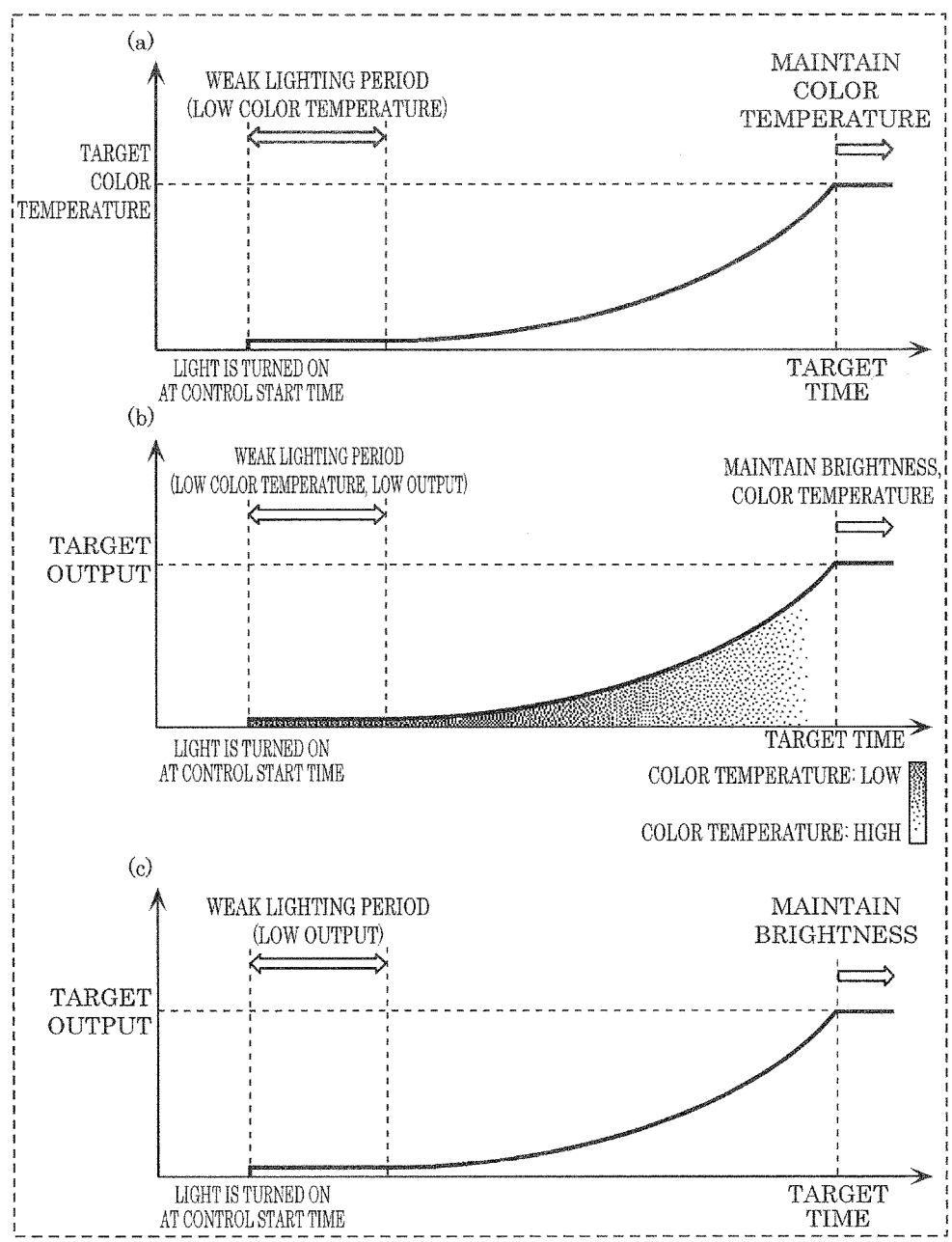
FIG. 6 is an explanatory diagram illustrating the color temperature and the brightness of light emitted by each illumination device included in the illumination system according to the embodiment.

(a) of FIG. 6 is an explanatory diagram illustrating a relationship between time and the color temperature of light emitted by each illumination device 3 included in illumination system 1 according to the present embodiment. (b) of FIG. 6 is an explanatory diagram illustrating, by the color temperature, a relationship among: the output of light emitted by each illumination device 3 included in illumination system 1 according to the present embodiment; time; and the color temperature of light emitted by each illumination device 3. (c) of FIG. 6 is an explanatory diagram illustrating a relationship between time and the output of light emitted by each illumination device 3 included in illumination system 1 according to the present embodiment.

Assumed here is the case where the estimated time of arrival of mobile body 100 is within the time period from the time of sunrise at the destination to the time of sunset at the destination. Assume in this case that the user is sleeping and illumination devices 3 are turned off until the target time. Additionally, assume that one or more target times are input in illumination system 1 in advance.

First, the user turns on the power of illumination system 1, so that illumination system 1 is activated and the flow illustrated in FIG. 5 starts. Controller 9 determines, based on the current time received from timer 7, whether or not it is the control start time before the target time (S11).

Next, when determining that it is the control start time (YES in S11), controller 9 turns on each illumination device 3 at the control start time as illustrated in FIG. 5 and FIG. 6 (S12). Here, controller 9 performs the weak lighting control to cause each illumination device 3 to emit weak light having a color temperature lower than the target color temperature (S12).

On the other hand, when determining that it is not the control start time (NO in S11), controller 9 repeats Step S11.

Controller 9 determines whether or not the time period from the control start time, that is, the current time, to the target time is longer than or equal to a predetermined period (S13).

When determining that the time period from the current time to the target time is longer than or equal to the predetermined period (YES in S13), controller 9 performs the weak lighting control for the first period (S14). The first period is an example of a weak lighting period illustrated in FIG. 6.

On the other hand, when determining that the time period from the current time to the target time is shorter than the predetermined period (NO in S13), controller 9 performs the weak lighting control for the second period (S18). The second period is an example of the weak lighting period illustrated in FIG. 6. Then, the processing proceeds to Step S15.

Next, as illustrated in FIG. 5 and (a) and (b) of FIG. 6, after finishing the weak lighting control performed for the first period or the second period, controller 9 performs the color temperature increase control of increasing the color temperature of the light emitted by illumination devices 3 to the target color temperature with a lapse of time so that the color temperature reaches the target color temperature at the estimated time of arrival (S15).

Further, as illustrated in FIG. 5 and (c) of FIG. 6, after finishing the weak lighting control performed for the first period or the second period, controller 9 performs the output increase control to gradually increase the brightness of the light emitted by illumination devices 3 with a lapse of time so that the brightness reaches the target output at the estimated time of arrival (S16). Note that Step S15 and Step S16 may be performed simultaneously, or may be performed in reverse order.

Next, as illustrated in FIG. 5 and (a) and (b) of FIG. 6, after finishing the color temperature increase control, controller 9 performs the color temperature maintaining control of maintaining the color temperature of the light emitted by illumination devices 3 at the target color temperature (S17). In Step S17, the brightness of the light emitted by illumination devices 3 may be maintained at the target output. Then, the flow is finished and controller 9 returns to the start to control the plurality of illumination devices 3 based on a subsequent target time. Note that the maintaining period during which illumination devices 3 continue emitting light having the target color temperature may finish at the subsequent target time or may be a predetermined period; it may be changed as appropriate depending on the usage.

In such a manner as described, it is possible to provide the user with a pleasant lighting environment by changing the target color temperature according to the time period from the estimated time of arrival to the time of sunset and controlling the color temperature of the light emitted by illumination devices 3 according to the estimated time of arrival of mobile body 100.

[Result of Experiment]

The following experiment was conducted in order to wake up a user pleasantly.

Figure 7:
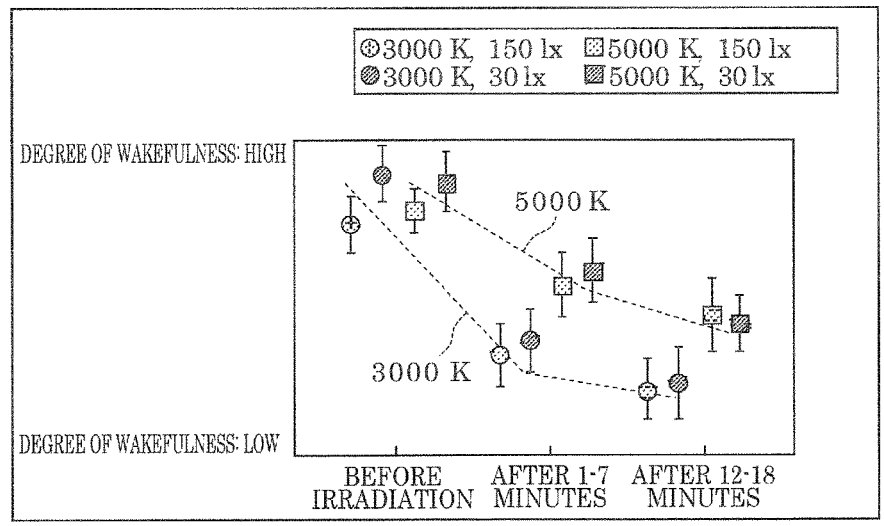
FIG. 7 is a graph illustrating a relationship between time and the degree of wakefulness achieved by color temperature control.

FIG. 7 is a graph illustrating a relationship between time and the degree of wakefulness achieved by the color temperature control. FIG. 7 illustrates the result of a physiological evaluation experiment conducted on eight test subjects using the color temperature and the illuminance before sleep as parameters.

In FIG. 7, the vertical axis indicates the degree of wakefulness and the horizontal axis indicates time. The degree of wakefulness was measured in each of the case where the illumination in the aircraft had a color temperature of 3000 K and the case where the illumination in the aircraft had a color temperature of 5000 K. The degree of wakefulness was measured in each of the case where the illumination in the aircraft had an illuminance of 30 lx and the case where the illumination in the aircraft had an illuminance of 150 lx. Note that the degree of wakefulness is determined according to the center frequency of the brain waves of each test subject; the higher the center frequency of the brain waves is, the higher the degree of wakefulness is.

It can be seen from FIG. 7 that the impact on the degree of wakefulness given by the color temperature is greater than the impact given by the illuminance. Specifically, it can be seen that the degree of wakefulness tends to decrease more when the color temperature is 3000 K than when the color temperature is 5000 K.

Based on this result, 5000 K is set as the target color temperature and 3000 K is set as the color temperature for weak lighting in the present embodiment.

Users often face upward when sleeping on an aircraft. Thus, controller 9 effectively increases the degree of wakefulness of the user by increasing the color temperature of the light emitted by illumination devices 3 to the target color temperature with a lapse of time.

[Advantageous Effects]

Next, advantageous effects produced by illumination system 1 and mobile body 100 according to the present embodiment are described.

As described above, illumination system 1 according to the present embodiment includes: illumination device 3; time setter 5 that sets a target time; and controller 9 that controls a color temperature of light emitted by illumination device 3. Controller 9 determines a target color temperature according to the target time, and causes the color temperature of the light emitted by illumination device 3 to be the target color temperature at the target time.

According to this, controller 9 causes the color temperature of the light emitted by illumination device 3 to be the target color temperature determined according to the target time set by time setter 5. Thus, by controlling the color temperature of the light emitted by illumination device 3 from the control start time before the target time, the sleep state of the user who is asleep can be lightened, for example, thereby making it possible to prompt the user to wake up at the target time that is a wake-up time. As a result, the user can wake up pleasantly at the target time.

Accordingly, it is possible to provide a lighting environment appropriate to the user after wake-up, in terms of the biological rhythm.

In particular, with the illumination system, controller 9 may control the color temperature of the light emitted by illumination device 3, in accordance with the reaction curve illustrated in FIG. 11. In this case, the user can wake up pleasantly in a more preferable state.

In addition, mobile body 100 according to the present embodiment includes the illumination system.

Mobile body 100 using illumination system 1 also produces the same advantageous effects. Illumination system 1 is suitable to mobile body 100.

In illumination system 1 according to the present embodiment, controller 9 further performs color temperature increase control of increasing the color temperature of the light emitted by illumination device 3 to the target color temperature with a lapse of time.

According to this, by increasing the color temperature of the light emitted by illumination device 3 from the control start time before the target time, controller 9 can, for example, lighten the sleep state of the user who is asleep, thereby making it possible to prompt the user to wake up at the target time that is a wake-up time. As a result, the user can wake up pleasantly at the target time.

In illumination system 1 according to the present embodiment, when performing the color temperature increase control, controller 9 gradually increases the color temperature of the light emitted by illumination device 3.

According to this, since controller 9 gradually increases the color temperature of the light emitted by illumination device 3, the sleep state of the user who is asleep is lightened, for example, thereby allowing the user to wake up more pleasantly at the target time.

In illumination system 1 according to the present embodiment, after performing the color temperature increase control, controller 9 further performs color temperature maintaining control of maintaining the color temperature of the light emitted by illumination device 3 at the target color temperature.

According to this, since controller 9 maintains the color temperature of the light emitted by illumination device 3 at the target color temperature, it is possible to more effectively prompt the user to wake up at the target time that is a wake-up time. As a result, the user can wake up more pleasantly at the target time.

In illumination system 1 according to the present embodiment, controller 9 further performs output increase control of increasing a brightness of the light emitted by illumination device 3 to a target output with a lapse of time.

According to this, since controller 9 increases the brightness of the light emitted by illumination device 3, the sleep state of the user who is asleep is lightened, for example, thereby allowing the user to wake up more pleasantly at the target time.

In illumination system 1 according to the present embodiment, when performing the output increase control, controller 9 gradually increases the brightness of the light emitted by illumination device 3.

According to this, since controller 9 gradually increases the brightness of the light emitted by illumination device 3, the sleep state of the user who is asleep is lightened, for example, thereby allowing the user to wake up more pleasantly at the target time.

In illumination system 1 according to the present embodiment, before performing the color temperature increase control, controller 9 further performs weak lighting control of causing illumination device 3 to emit light having a brightness lower than the target output and a color temperature lower than the target color temperature.

If the light emitted by illumination device 3 is too bright, the user may wake up before the target time. With illumination system 1, however, controller 9 causes illumination device 3 to emit weak light before the color temperature increase control, and thus, the user can wake up more pleasantly at the target time.

Illumination system 1 according to the present embodiment further includes timer 7 that outputs a current time to controller 9. Controller 9 calculates a sleep period from a bedtime to the target time using timer 7, and determines a time period during which the weak lighting control is to be performed, based on the sleep period.

According to this, controller 9 determines, based on the sleep period from the bedtime to the target time, the time period during which the weak lighting control is to be performed, and thus it is possible to prompt the user to wake up at the target time according to the sleep period.

Illumination system 1 according to the present embodiment further includes timer 7 that outputs a current time to controller 9. Controller 9 determines a control period based on a time period from the current time received from timer 7 to the target time.

In illumination system 1 according to the present embodiment, controller 9 determines to perform the weak lighting control for a first period when a time period from a current time to the target time is longer than or equal to a predetermined period, and determines to perform the weak lighting control for a second period shorter than the first period when the time period from the current time to the target time is shorter than the predetermined period.

Illumination system 1 according to the present embodiment further includes storage 11 that stores a table in which a target color temperature is associated with the target time. Controller 9 determines a target color temperature corresponding to the target time based on the table stored in the storage.

In illumination system 1 according to the present embodiment, time setter 5 sets a plurality of target times. Controller 9 performs the color temperature maintaining control on illumination device 3 from a first target time to a second target time. Here, the first target time is one of the plurality of target times, and the second target time is another one of the plurality of target times which is set by the time setter as a target time subsequent to the first target time.

In mobile body 100 according to the present embodiment, the target time is an estimated time of arrival at which mobile body 100 is to arrive at a destination.

According to this, the user can pleasantly wake up at the estimated time of arrival of mobile body 100.

In mobile body 100 according to the present embodiment, when the estimated time of arrival is within a time period from a time of sunrise at the destination to a time of sunset at the destination, controller 9 decreases the target color temperature according to a time period from the estimated time of arrival to the time of sunset.

According to this, when mobile body 100 is to arrive at the destination in the daytime, controller 9 decreases the target color temperature according to the time period from the estimated time of arrival to the time of sunset. Specifically, for example, if the time period from the estimated time of arrival to the time of sunset at the destination is short, it means that the sun will set shortly, and therefore, controller 9 decreases the target color temperature to inhibit the user's awakening. Further, for example, if the time period from the estimated time of arrival to the time of sunset at the destination is long, it means that there is a long period of time before the sunset, and therefore, controller 9 slightly decreases the target color temperature. In such a manner, controller 9 decreases the target color temperature according to the above time period, and thus, illumination that induces the user's sleep after the sunset can be provided if the time period up to the sunset is short, whereas illumination that awakes the user can be provided if the time period up to the sunset is long. As a result, it is possible to provide the user with a pleasant lighting environment by controlling the color temperature of the light emitted by illumination device 3 according to the estimated time of arrival of mobile body 100.

In mobile body 100 according to the present embodiment, when the estimated time of arrival is within a time period from a time of sunset at the destination to a time of sunrise at the destination, controller 9 causes the color temperature of the light emitted by illumination device 3 to be the target color temperature.

According to this, since controller 9 causes the color temperature to be the determined target color temperature even when mobile body 100 is to arrive at the destination in the nighttime, the sleep state of the user who is asleep is lightened, for example, thereby making it possible to prompt the user to wake up at the target time that is a wake-up time.

In mobile body 100 according to the present embodiment, controller 9 decreases the target color temperature as a time period from the estimated time of arrival to the time of sunrise at the destination becomes longer than a time period from the time of sunset at the destination to the estimated time of arrival. Further, controller 9 decreases the target color temperature to a lowest target color temperature when the time period from the time of sunset at the destination to the estimated time of arrival is approximately equal to the time period from the estimated time of arrival to the time of sunrise at the destination. Further, controller 9 increases the target color temperature as the time period from the estimated time of arrival to the time of sunrise at the destination becomes shorter than the time period from the time of sunset at the destination to the estimated time of arrival.

According to this configuration, when mobile body 100 arrives at the destination in a time period from the sunset to the midnight, the target color temperature is decreased to the lowest target color temperature or the target color temperature is gradually decreased so that the user is awoken but will be able to easily have a sleep again at the destination, for example. When mobile body 100 arrives at the destination in a time period from the midnight to the dawn, the target color temperature is gradually increased to a target color temperature higher than the target color temperature when mobile body 100 arrives at the destination in the nighttime before midnight so that the user is awoken as if in the morning. In such a manner, by adjusting the target color temperature according to the time period from the estimated time of arrival to the time of sunset, it is possible to inhibit disturbance of the user's biological rhythm.

Other Embodiments

Hereinbefore, an embodiment of the present disclosure has been described; however, the present disclosure is not limited to this embodiment.

For example, the present disclosure may be implemented as a mobile body (for example, an aircraft or a train) including the above-described illumination system or may be implemented in a facility such as a residence or a hotel.

Figure 8:
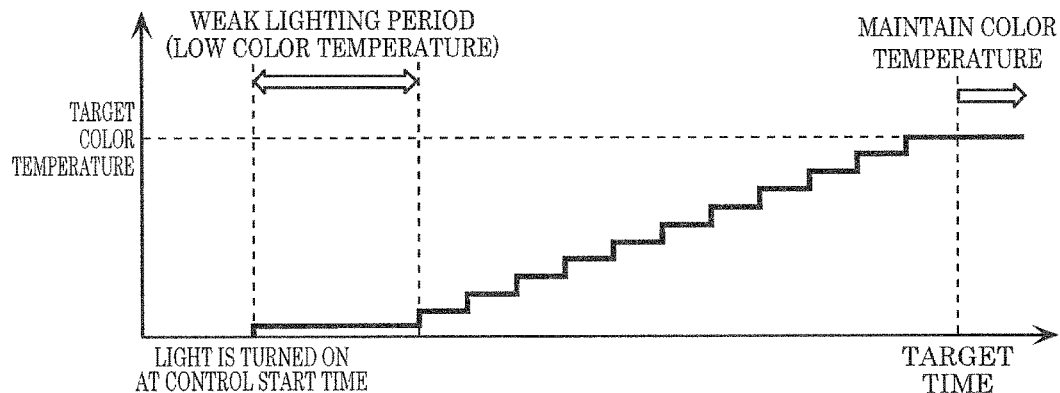
FIG. 8 is an explanatory diagram illustrating the color temperature of light emitted by each illumination device included in an illumination system according to a variation.

In relation to the illumination system described in the above embodiment, FIG. 8 is an explanatory diagram illustrating the color temperature of light emitted by each illumination device included in an illumination system according to a variation. As illustrated in FIG. 8, the controller may perform the color temperature increase control by increasing the color temperature of light emitted by each illumination device to the target color temperature in a stepwise manner.

When the estimated time of arrival of the mobile body described in the above embodiment is within a time period from the time of sunset at the destination to the time of sunrise at the destination, the controller may decrease the target color temperature with an increase in the time period from the time of sunset at the destination to the estimated time of arrival. In this case, the controller awakes the user in a manner that the user will be able to easily have a sleep at the destination, for example, rather than causing the user to be awake as in the daytime. Accordingly, the illumination system allows the user to easily have a sleep even after the user wakes up at the target time. As a result, it is possible to inhibit disturbance of the user's biological rhythm. Note that the illumination system may be capable of determining the target color temperature according to the target time for each user or each illumination device that is freely selected.

Figure 9:
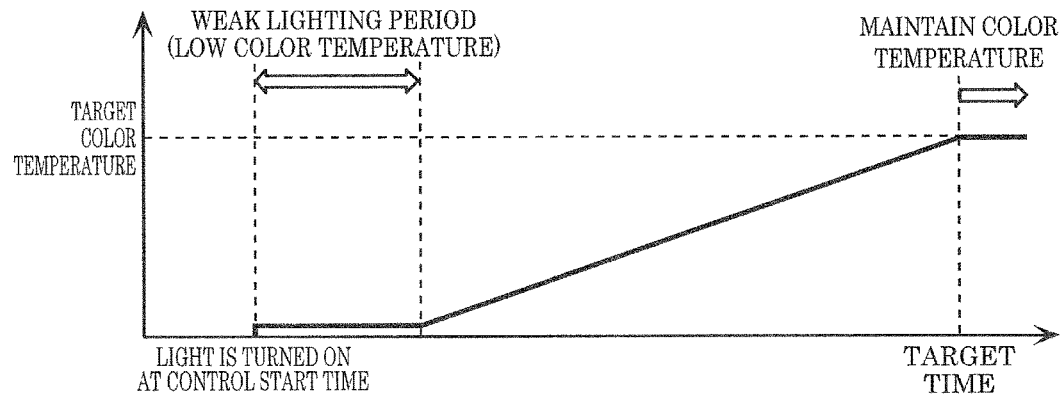
FIG. 9 is an explanatory diagram illustrating the color temperature of light emitted by each illumination device included in an illumination system according to a variation.

Further, in relation to the illumination system described in the above embodiment, FIG. 9 is an explanatory diagram illustrating the color temperature of light emitted by each illumination device included in an illumination system according to a variation. As illustrated in FIG. 9, the controller may perform the color temperature increase control by linearly increasing the color temperature of light emitted by each illumination device to the target color temperature. Note that the increase curve of the color temperature of light emitted by each illumination device, which is increased by the controller performing the temperature increase control, is not limited to those illustrated in FIG. 6, FIG. 8, and FIG. 9, and may be a different curve.

Moreover, with the illumination system described in the above embodiment, when the estimated time of arrival is within a time period from the time of sunset at the destination to the time of sunrise at the destination, the target color temperature may be increased/decreased linearly or curvilinearly. That is to say, the way in which the target color temperature is increased/decreased is not particularly limited.

Although the light emitter described in the above embodiment includes an LED, such a configuration is one example. A fluorescent tube, a metal halide lamp, a sodium lamp, a halogen lamp, a xenon lamp, a neon tube, etc. may be used as the light emitter. Further, inorganic electroluminescence, organic electroluminescence, chemiluminescence, a semiconductor laser, etc. may be used for the light emitter. In addition, the light emitter may emit light having a desired color using a spectral filter, for example. The light emitter may be configured in any manner as long as the control (dimming control or toning control) necessary for the illumination control is possible.

Furthermore, the general or specific aspects of the present disclosure may be implemented by a system, a method, an integrated circuit, a computer program, or a computer-readable recording medium such as a compact disc read only memory (CD-ROM), or by any combination of a system, a method, an integrated circuit, a computer program, and a recording medium. For example, the present disclosure may be implemented as an illumination control method, a program for causing a computer to execute an illumination control method, or the controller according to the above embodiment (a control device).

Moreover, the division of the functional blocks in the block diagram is one example. A plurality of functional blocks may be implemented as one functional block, or one functional block may be divided into a plurality of functional blocks, or part of one function may be transferred to another functional block. In addition, functions of a plurality of functional blocks having similar functions may be processed in parallel or by time-division by a single hardware or software product.

While the foregoing has described the illumination system according to one or more aspects of the present disclosure based on an embodiment, the present disclosure is not limited to this embodiment. Various modifications to the present embodiment that are conceivable to those skilled in the art, as well as embodiments resulting from combinations of structural elements of different embodiments may be included within the scope of one or more aspects of the present disclosure, as long as such modifications and embodiments do not depart from the essence of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. An illumination system, comprising:
an illumination device;
a time setter that sets a target time; and
a controller that controls a color temperature of light emitted by the illumination device,
wherein the controller:
determines a target color temperature according to the target time, and causes the color temperature of the light emitted by the illumination device to be the target color temperature at the target time,
performs color temperature increase control of increasing the color temperature of the light emitted by the illumination device to the target color temperature with a lapse of time,
performs output increase control of increasing a brightness of the light emitted by the illumination device to a target output with a lapse of time, and
before performing the color temperature increase control, performs weak lighting control of causing the illumination device to emit light having a brightness lower than the target output and a color temperature lower than the target color temperature.

2. The illumination system according to claim 1, wherein when performing the color temperature increase control, the controller gradually increases the color temperature of the light emitted by the illumination device.

3. The illumination system according to claim 1, wherein after performing the color temperature increase control, the controller further performs color temperature maintaining control of maintaining the color temperature of the light emitted by the illumination device at the target color temperature.

4. The illumination system according to claim 3, wherein the time setter sets a plurality of target times, and
the controller performs the color temperature maintaining control on the illumination device from a first target time to a second target time, the first target time being one of the plurality of target times, the second target time being another one of the plurality of target times which is set by the time setter as a target time subsequent to the first target time.

5. The illumination system according to claim 1, wherein when performing the output increase control, the controller gradually increases the brightness of the light emitted by the illumination device.

6. The illumination system according to claim 1, further comprising:
a timer that outputs a current time to the controller,
wherein the controller calculates a sleep period from a bedtime to the target time using the timer, and determines a time period during which the weak lighting control is to be performed, based on the sleep period.

7. The illumination system according to claim 1, further comprising:
a timer that outputs a current time to the controller,
wherein the controller determines a control period based on a time period from the current time received from the timer to the target time.

8. The illumination system according to claim 1, wherein the controller:
determines to perform the weak lighting control for a first period when a time period from a current time to the target time is longer than or equal to a predetermined period; and
determines to perform the weak lighting control for a second period shorter than the first period when the time period from the current time to the target time is shorter than the predetermined period.

9. The illumination system according to claim 1, further comprising:
a storage that stores a table in which a target color temperature is associated with the target time,
wherein the controller determines a target color temperature corresponding to the target time based on the table stored in the storage.

10. A mobile body, comprising:
an illumination system including:
an illumination device;
a time setter that sets a target time; and
a controller that controls a color temperature of light emitted by the illumination device,
wherein the controller determines a target color temperature according to the target time, and causes the color temperature of the light emitted by the illumination device to be the target color temperature at the target time,
the target time is an estimated time of arrival at which the mobile body is to arrive at a destination,
when the estimated time of arrival is within a time period from a time of sunset at the destination to a time of sunrise at the destination, the controller causes the color temperature of the light emitted by the illumination device to be the target color temperature, and
the controller:
decreases the target color temperature as a time period from the estimated time of arrival to the time of sunrise at the destination becomes longer than a time period from the time of sunset at the destination to the estimated time of arrival;
decreases the target color temperature to a lowest target color temperature when the time period from the time of sunset at the destination to the estimated time of arrival is approximately equal to the time period from the estimated time of arrival to the time of sunrise at the destination; and
increases the target color temperature as the time period from the estimated time of arrival to the time of sunrise at the destination becomes shorter than the time period from the time of sunset at the destination to the estimated time of arrival.

11. The mobile body according to claim 10, wherein when the estimated time of arrival is within a time period from a time of sunrise at the destination to a time of sunset at the destination, the controller decreases the target color temperature according to a time period from the estimated time of arrival to the time of sunset.

12. The mobile body according to claim 10, wherein the controller decreases the target color temperature with an increase in a time period from the time of sunset at the destination to the estimated time of arrival.

* * * * *